US011298089B2

(12) United States Patent
Erler et al.

(10) Patent No.: US 11,298,089 B2
(45) Date of Patent: Apr. 12, 2022

(54) X-RAY EXAMINATION ARRANGEMENT AND METHOD FOR OPERATING AN X-RAY EXAMINATION ARRANGEMENT

(71) Applicant: Carl Zeiss Industrielle Messtechnik GmbH, Oberkochen (DE)

(72) Inventors: Marco Erler, Oberkochen (DE); Daniel Weiss, Essingen-Forst (DE); Martin Krenkel, Aalen (DE); Wolfgang Kimmig, Aalen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 0 days.

(21) Appl. No.: 16/798,348

(22) Filed: Feb. 22, 2020

(65) Prior Publication Data
US 2020/0268326 A1    Aug. 27, 2020

(30) Foreign Application Priority Data
Feb. 22, 2019   (DE) ...................... 10 2019 202 452.1

(51) Int. Cl.
*A61B 6/00*      (2006.01)
*A61B 6/03*      (2006.01)

(52) U.S. Cl.
CPC ............ *A61B 6/035* (2013.01); *A61B 6/4028* (2013.01); *A61B 6/52* (2013.01); *A61B 6/582* (2013.01)

(58) Field of Classification Search
CPC ....... A61B 6/032; A61B 6/035; A61B 6/4028; A61B 6/4266; A61B 6/52; A61B 6/5205; A61B 6/5241; A61B 6/582; G01N 2223/419; G01N 2223/501; G01N 23/04
See application file for complete search history.

(56) References Cited

U.S. PATENT DOCUMENTS

| | | | |
|---|---|---|---|
| 5,550,378 A | 8/1996 | Skillicorn et al. | |
| 5,901,196 A | 5/1999 | Sauer et al. | |
| 6,236,704 B1* | 5/2001 | Navab .................. | A61B 6/4441 378/4 |
| 6,292,529 B1 | 9/2001 | Marcovici et al. | |

(Continued)

FOREIGN PATENT DOCUMENTS

| | | |
|---|---|---|
| DE | 19844955 A1 | 4/1999 |
| DE | 102008048688 B4 | 8/2011 |

(Continued)

*Primary Examiner* — Dani Fox
(74) *Attorney, Agent, or Firm* — Falk Ewers; Ewers IP Law PLLC

(57) ABSTRACT

An x-ray examination arrangement includes an x-ray radiation source arranged at a source position, at least two x-ray detectors having active detector areas and being arranged such that the active detector areas capture different solid angle ranges with respect to x-ray radiation produced by the x-ray radiation source and emanating from the source position, and a control device configured to calculate a projection onto a virtual detector plane based on radiographs respectively captured by the at least two x-ray detectors and spatial poses of the at least two x-ray detectors relative to the source position, and provide a combined radiograph for the virtual detector plane based on the projection. In addition, a method for operating the x-ray examination arrangement and a computed tomography device are provided.

10 Claims, 3 Drawing Sheets

(56) References Cited

U.S. PATENT DOCUMENTS

| | | |
|---|---|---|
| 6,389,102 B2 | 5/2002 | Mazor et al. |
| 6,546,068 B1 * | 4/2003 | Shimura ............... A61B 6/032 |
| | | 378/19 |
| 7,711,083 B2 * | 5/2010 | Heigl .................. G01N 23/046 |
| | | 378/20 |
| 8,009,796 B2 | 8/2011 | Popescu et al. |
| 8,971,484 B2 | 3/2015 | Beckmann et al. |
| 2004/0228453 A1 * | 11/2004 | Dobbs ................... A61B 6/463 |
| | | 378/210 |

FOREIGN PATENT DOCUMENTS

| | | |
|---|---|---|
| DE | 112012004856 T5 | 12/2014 |
| DE | 102006041033 B4 | 1/2017 |
| DE | 102018201324 A1 | 8/2019 |
| JP | 2000201920 A | 7/2000 |

\* cited by examiner

X-RAY EXAMINATION ARRANGEMENT AND METHOD FOR OPERATING AN X-RAY EXAMINATION ARRANGEMENT

CROSS REFERENCE TO RELATED APPLICATIONS

This application claims priority to German patent application DE 10 2019 202 452.1, filed Feb. 22, 2019, the entire content of which is incorporated herein by reference.

TECHNICAL FIELD

The disclosure relates to an x-ray examination arrangement and a method for operating an x-ray examination arrangement. Further, the disclosure relates to a computed tomography device.

BACKGROUND

In computed tomography, use is made of x-ray examination arrangements including an x-ray source and an x-ray detector. Here, a significant feature of such an x-ray examination arrangement is a size of an active detector area of the x-ray detector. A solid angle captured by an x-ray detector, and also the absolute size of the examined components, can be larger with a larger active detector area of the x-ray detector. However, a maximum size of the active detector area of the x-ray detector is limited by a readout process of the individual detector elements. Since x-ray detectors, in respect of individual detector elements, are read element-by-element in rows or columns, there is always a compromise between a size of the active detector area and a readout speed at the same resolution. Although x-ray detectors with large active detector areas with a high resolution and fast readout times can be produced as a matter of principle, these are more complicated to produce on account of a more complex design, in particular more complex readout electronics, and therefore costly.

DE 10 2008 048 688 B4 describes an x-ray CT system. The x-ray CT system serves to produce tomographic phase-contrast or dark-field recordings, and is operated as a Talbot interferometer. The x-ray CT system includes a plurality of detector modules, which are arranged next to one another. Each of the detector modules includes a plurality of detector elements. Phase gratings for producing interference patterns are arranged in front of the detectors.

DE 11 2012 004 856 T5 describes a system, an apparatus, and a method for fast and space-saving screening of objects, in particular luggage, by x-ray tomography. What is described is that an object to be examined is examined by a plurality of x-ray source arrays and a plurality of x-ray detector arrays, and a three-dimensional reconstruction is produced on the basis of the projections of the object.

SUMMARY

It is an object of the disclosure to develop an x-ray examination arrangement and a method for operating an x-ray examination arrangement, with which larger active detector areas can be provided with less outlay and more cost effectively.

The object is achieved by an x-ray examination arrangement and a method for operating an x-ray examination arrangement as described herein.

A general concept of the disclosure is to develop a virtual x-ray detector by virtue of combining at least two x-ray detectors. The virtual x-ray detector has a larger active detector area than the individual x-ray detectors without, however, having the disadvantages in respect of readout speed and/or resolution, as are described at the outset. The virtual x-ray detector is developed by virtue of a projection onto a virtual detector plane being calculated by a control device of the x-ray examination arrangement on the basis of radiographs respectively captured by the at least two x-ray detectors and the spatial poses of the at least two x-ray detectors relative to a source position of an x-ray radiation source. Subsequently, a combined radiograph for the virtual detector plane is provided on the basis of this projection onto the virtual detector plane. The combined radiograph is effectively larger than the individual radiographs of the at least two x-ray detectors, i.e., the combined radiograph images a larger solid angle with, at the same time, an unchanging resolution and, in each case, an unchanging readout speed.

Moreover, an advantage of the disclosure is that cost-effective x-ray detectors can be used as these can easily be combined with one another in order to effectively create a larger active detector area. The complicated and costly production of an individual x-ray detector with a large active detector area with a high resolution and a fast readout speed can be dispensed with or circumvented as a result thereof. As a result of the provision of a combined radiograph, which corresponds to a virtual x-ray detector or a virtual detector plane, further processing, for example for the three-dimensional reconstruction of a measured object, can be implemented in conventional fashion.

In particular, an x-ray examination arrangement is created, including an x-ray radiation source at a source position, at least two x-ray detectors, and a control device, wherein the at least two x-ray detectors are arranged in such a way that active detector areas of the at least two x-ray detectors are able to capture different solid angle ranges with respect to x-ray radiation produced by the x-ray radiation source and emanating from the source position, wherein the control device is configured to calculate a projection onto a virtual detector plane on the basis of radiographs respectively captured by the at least two x-ray detectors and the spatial poses of the at least two x-ray detectors relative to the source position and to provide a combined radiograph for the virtual detector plane on the basis of the projection.

Further, in particular, a method for operating an x-ray examination arrangement is made available, wherein the x-ray examination arrangement includes an x-ray radiation source at a source position, at least two x-ray detectors, and a control device, wherein the at least two x-ray detectors are arranged in such a way that active detector areas of the at least two x-ray detectors capture different solid angle ranges with respect to x-ray radiation produced by the x-ray radiation source and emanating from the source position, and wherein the control device is used to calculate a projection onto a virtual detector plane on the basis of radiographs respectively captured by the at least two x-ray detectors and the spatial poses of the at least two x-ray detectors relative to the source position and to provide a combined radiograph for the virtual detector plane on the basis of the projection.

Further, a computed tomography device includes at least one x-ray examination arrangement according to an exemplary embodiment, wherein the computed tomography device is configured to carry out a three-dimensional reconstruction, at least also on the basis of the provided combined radiograph.

A respective spatial pose of the at least two x-ray detectors can be ascertained with the aid of known methods. Here, the spatial pose relates, in particular, to the geometric arrangement relative to the x-ray radiation source and a test object, i.e., in relation to the beam path of the x-ray examination arrangement or of the computed tomography device, in which the x-ray examination arrangement is arranged. By way of example, a radiograph of a known reference object, arranged in a beam path between the x-ray radiation source and the at least two x-ray detectors, is captured by each of the at least two x-ray detectors for the purposes of determining the spatial pose. The spatial pose, i.e., an orientation and a position, of the respective x-ray detector or its active detector area can be ascertained from the respective radiograph in the case of known properties of the x-ray radiation and of the reference object. The ascertained spatial poses of the x-ray detectors or associated active detector areas subsequently form a basis for the projection.

The projection, in particular the perspective projection, onto the virtual detector plane is implemented, in particular, by virtue of, with reference to a projection straight line emanating from the source position, an image value at a point of intersection of the projection straight line with the at least two x-ray detectors being ascertained and this ascertained image value being subsequently projected onto the virtual detector plane along the projection straight line. Here, provision can be made for an interpolation to be carried out with adjacent image values being taken into account in order to take account or merge different scanning of the x-ray detector and the virtual detector plane. Should points of intersection with a plurality of x-ray detectors lie on the projection straight line, the associated image values are taken into account by way of a weighted sum, for example.

The control device can be embodied as a combination of hardware and software, for example as program code that is executed on a microcontroller or microprocessor.

In one exemplary embodiment, provision is made for the at least two x-ray detectors to at least partly overlap in relation to a propagation direction of the x-ray radiation. Expressed in simple terms, one of the at least two x-ray detectors is arranged partly in front of the others of the at least two x-ray detectors in relation to the direction of propagation. Here, an overlap region is chosen in such a way, in particular, that the active detector areas of the at least two x-ray detectors overlap one another in edge regions, at least in relation to the direction of propagation of the x-ray radiation, such that there are no solid angle ranges between the at least two x-ray detectors that are not captured. In particular, part of a detector housing surrounding the active detector area of a front x-ray detector may be arranged in front of an active detector area of a back x-ray detector. In the overlap region, pixels of both the front x-ray detector and the back x-ray detector are taken into account during the projection. By way of example, the respective image values are combined by a weighted sum, wherein weighting coefficients are chosen in such a way, for example, that there is a linear transition from image values of the front x-ray detector to image values of the back x-ray detector, i.e., when the overlap region between the x-ray detectors is swept, a weighting coefficient of the one x-ray detector increases linearly from 0% to 100% while a weighting coefficient of the other x-ray detector drops linearly from 100% to 0%.

In one exemplary embodiment, provision is made for the at least two x-ray detectors to be arranged relative to one another in such a way that actuation electronics of the x-ray detectors are arranged outside of an overlap region of the x-ray detectors. This can prevent the actuation electronics of one detector disturbing the capture of a radiograph by another x-ray detector. Depending on the type of employed x-ray detectors and depending on a position of the actuation electronics, it is possible to form arbitrarily large arrangements with arbitrarily many x-ray detectors. If actuation electronics are only arranged at an edge of the x-ray detector, it is possible, in principle, to form arrangements with 2×n x-ray detectors, i.e., for example, two rows of n x-ray detectors each, arranged above one another. Here, the actuation electronics of the x-ray detectors of the upper row are arranged at the upper edge and the actuation electronics of the x-ray detectors of the lower row are arranged at the lower edge. By contrast, if the x-ray detectors include actuation electronics at more than one edge, this reduces the options for arrangement and hence also reduces a possible size of the combined active detector areas and of the combined radiograph. By way of example, if actuation electronics are located at two adjacent edges of the x-ray detectors, a 2×2 arrangement is possible if the actuation electronics are arranged at outer edges of the 2×2 arrangement.

In a further exemplary embodiment, provision is made for the at least two x-ray detectors to be arranged in such a way that planes of at least two of the x-ray detectors have an angle with respect to one another, said planes corresponding to the active detector areas, and/or that x-ray radiation emanating from the x-ray radiation source is incident on the planes or the active detector areas in perpendicular fashion, at least in relation to a center point of the active detector areas. If x-ray detectors are arranged next to one another such that the planes coinciding with the active detector areas are parallel to one another, it is possible to capture a larger aperture angle of the x-ray radiation but an angle of incidence of the x-ray radiation on the active detector area in an outer edge region is smaller than in the region of the optical axis or at a center point of the active detector area. This leads to a reduced resolution in the edge region since the radiation does not strike the active detector area in perpendicular fashion there. The cause of this is that x-ray photons in the x-ray detector are converted into visible electromagnetic radiation in the x-ray detector by scintillation layers, which are arranged upstream of the detector elements (e.g., photodiodes). The visible electromagnetic radiation subsequently propagates isotropically. In the case of a flat angle of incidence, a scintillation layer passed by an x-ray photon is effectively thicker, and so there is an increase in the probability that visible electromagnetic radiation produced by the x-ray photon is also detected in an adjacent detector element. Overall, this leads to a reduced resolution. In order to compensate such an effect, the active detector area of the x-ray detector can be tilted in relation to the optical axis, in particular to such an extent that x-ray radiation emanating from the x-ray radiation source is incident in perpendicular fashion on the active detector area, at least in relation to a center point of said active detector area. This can compensate the loss of resolution in the edge region or a mean resolution of an x-ray detector can be set and improved.

In one exemplary embodiment, provision can be made for the control device to be configured to correct a disturbance, caused by at least one of the x-ray detectors, in the captured radiographs and/or in the combined radiograph. In the simplest case, an "offset/gain" correction (also referred to as a "flat-field correction") is carried out to this end. This is implemented in such a way that the "gain" value in the case of an activated x-ray source is determined for the arrangement of the at least two x-ray detectors chosen in the x-ray examination arrangement. If one of the x-ray detectors, for example by way of a housing edge, is arranged in front of an active detector area of another x-ray detector, this housing edge is imaged in an overlap region in a radiograph captured by the latter x-ray detector. This is also reflected in the respective "gain" values of pixels lying in the overlap region, and so a constant or linear effect of the front x-ray detector on the back x-ray detector can be at least partly corrected by the "offset/gain" correction.

Moreover, nonlinear effects also occur, however. These cannot be corrected by the simple "offset/gain" correction. Here, a plurality of physical effects may have an influence on pixels of a captured radiograph. Since x-ray radiation has a broad energy spectrum and low-energy x-ray photons are absorbed more strongly than high-energy x-ray photons during the passage through a front x-ray detector, beam hardening occurs. Further, x-ray radiation is scattered during the passage through the front x-ray detector, i.e., secondary x-ray photons that have different directions of propagation to the primary x-ray photons of the x-ray source are produced. The secondary x-ray photons are likewise captured by the back x-ray detector and falsify a captured radiograph.

Various methods can be used to correct the nonlinear effects, too. By way of example, there can be a model-based correction with the aid of a known reference object. As a result of a displacement of the reference object, pixel values with different greyscale values can be captured here for each detector element on account of different transmission lengths. This procedure can subsequently also be repeated for the overlap region, i.e., the reference object is imaged, at least in part, in the overlap region of the x-ray detectors. Corresponding image values of the detector elements are captured there. Since the properties of the reference object are known, non-disturbed image values can respectively be assigned to associated disturbed image values. Therefore, correction functions can be defined for the individual detector elements of the active detector areas, said correction functions being able to correct the disturbance detector element by detector element and on the basis of image values. Such a correction factor for a detector element in each case may be a polynomial function, for example, which is fitted to the respective pairs of disturbed and associated non-disturbed image values of the detector element. Here, additional provision can be made for information from respectively adjacent detector elements also to be taken into account in order also to take account of a scattering of the x-ray radiation.

Further, a machine learning-based correction may also be undertaken. In a manner analogous to the model-based correction, a machine learning-based correction can be implemented with the aid of a known reference object. As a result of a displacement of the reference object, pixel values with different greyscale values can be captured here for each detector element on account of different transmission lengths. This procedure can subsequently also be repeated for the overlap region, i.e., the reference object is imaged, at least in part, in the overlap region of the x-ray detectors. Corresponding image values of the detector elements are captured there. Since the properties of the reference object are known, non-disturbed image values can respectively be assigned to associated disturbed image values. In this way, target and actual data can be produced for the individual detector elements in each case. A correction model, for each detector element in particular, is trained by known machine learning methods on the basis of these target and actual data. The trained correction model is then applied to subsequent actual data, i.e., captured radiographs.

In one exemplary embodiment, provision is made for the control device to be further configured to synchronize the at least two x-ray detectors with respect to respective capture times of the radiographs and/or to adapt capture times of picture elements (pixels) in the radiographs. Firstly, x-ray detectors are usually triggered at a trigger input for the purposes of starting a readout process. Then, the x-ray detectors can be synchronized, for example by virtue of the control device supplying the same readout trigger signal simultaneously to respective trigger inputs of the at least two x-ray detectors. Then, the readout of individual detector elements of the active detector areas is started simultaneously. This ensures that the combined radiograph has, at least on average, the same capture time. Further, provision can be made for trigger signals supplied by the x-ray detectors, which mark the start of the readout process, to be read and to be taken into account for the purposes of determining the captured time or times.

Since the readout of the individual detector elements is implemented row by row or column by column, i.e., successively and hence not simultaneously, all or at least some of the pixels in the radiograph may have different capture times. Therefore, provision can also be made for a capture time of the individual pixels to be adapted. By way of example, this is implemented by virtue of image values of pixels of radiographs captured at different adjacent times being interpolated to a mean capture time. What this can achieve is that all pixels of a radiograph of an x-ray detector or all pixels of radiographs of all x-ray detectors arranged in the x-ray examination arrangement have the same effective capture time. This is particularly advantageous if a rotating object is captured and examined by the x-ray examination arrangement since different capture times then correspond to different rotational angles of the object, which may lead to loss of sharpness of the captured radiographs. This effect can be compensated by the interpolation of the capture times.

In a further exemplary embodiment, provision is made for the control device to be configured to take a capture time of pixels of radiographs of the at least two x-ray detectors into account during the projection. By way of example, this is implemented by virtue of a respective capture time of a pixel being linked to a rotational angle of an object to be examined. By way of the rotational angle of the object, it is possible to take account of modified geometry information during the projection of the virtual detector plane. Depending on the capture time, there then is a change, in particular, of a projection angle for a respectively observed pixel or detector element. Such a procedure is particularly advantageous in the case of free-running, i.e., non-synchronized, x-ray detectors that capture a rotating test object. When projecting and creating the combined radiograph, the respective capture times of the individual pixels and the projection angles resulting therefrom are then taken into account, as a result of which, overall, a sharper combined radiograph can be provided.

In one exemplary embodiment, provision is made for the control device to be further configured to be able to set a pixel size in the combined radiograph. Since, as a rule, an interpolation is also carried out within the scope of the projection onto the virtual detector plane, the pixel element size of the associated combined radiograph can be chosen freely. Here, typically, a pixel size that corresponds to a maximum resolution (pixels per unit length) of the at least two x-ray detectors is chosen. Particularly in the case of mutually tilted x-ray detectors, the resolution that corresponds to the region of the x-ray detector that has the greatest resolution or the greatest scan density is respectively chosen in this case. It may also be advantageous to choose the pixel sizes of the virtual detector to be significantly smaller than the pixel sizes of the x-ray detectors. In this way, a loss of resolution linked to the interpolation, which could otherwise lead to a loss in the contrast of details in subsequently reconstructed volume data, can be compensated.

BRIEF DESCRIPTION OF THE DRAWINGS

The disclosure will now be described with reference to the drawings wherein.

DESCRIPTION OF EXEMPLARY EMBODIMENTS

Features relating to the configuration of the method emerge from the description of configurations of the x-ray examination arrangement. Here, the advantages of the method are the same as those of the x-ray examination arrangement.

Figure 1:
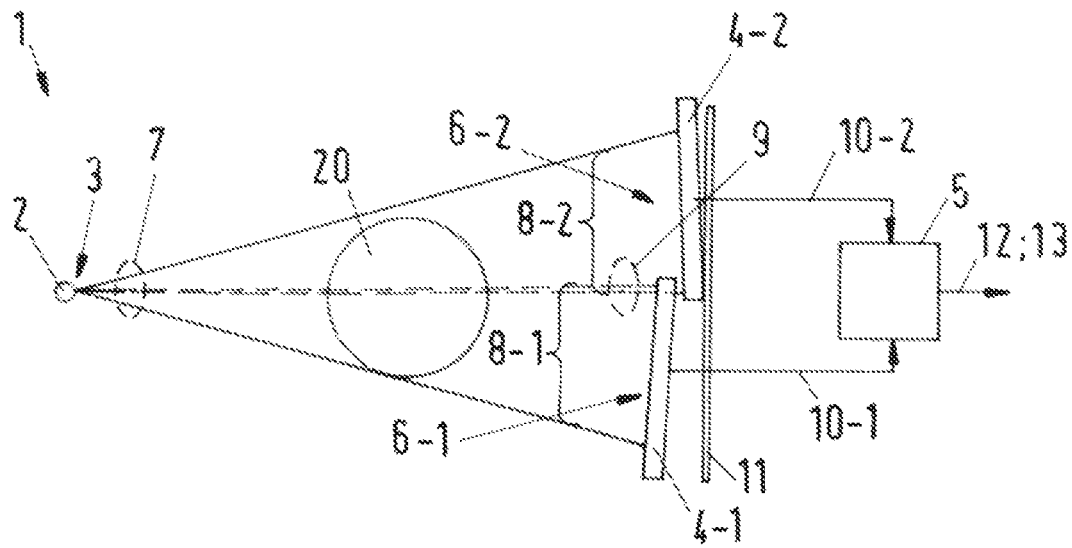
FIG. 1 shows a schematic illustration of an x-ray examination arrangement according to an exemplary embodiment of the disclosure.

FIG. 1 shows a schematic illustration of an x-ray examination arrangement 1. The x-ray examination arrangement 1 includes an x-ray radiation source 2 at a source position 3, two x-ray detectors 4-1 and 4-2, and a control device 5.

A test object can be positioned on a rotary stage 20 between the x-ray radiation source 2 and the x-ray detectors 4-1 and 4-2. In a computed tomography device, the test object can be measured tomographically and reconstructed in three dimensions with the aid of the x-ray examination arrangement 1.

The x-ray detectors 4-1 and 4-2 are arranged in such a way that active detector areas 6-1 and 6-2 of the x-ray detectors 4-1 and 4-2 are able to capture different solid angle ranges 8-1 and 8-2 with respect to x-ray radiation 7 produced by the x-ray radiation source 2 and emanating from the source position 3. The solid angle ranges 8-1 and 8-2 overlap in an overlap region 9 between the x-ray detectors 4-1 and 4-2 such that, in the overlap region 9, a portion of the solid angle ranges 8-1 and 8-2 is captured both by the front x-ray detector 4-1 and by the back x-ray detector 4-2.

The control device 5 is embodied as a combination of hardware and software, for example as program code that is executed on a microcontroller or microprocessor.

Radiographs 10-1 and 10-2 captured by the x-ray detectors 4-1 and 4-2 are supplied to the control device 5. The control device 5 calculates a projection onto a virtual detector plane 11 on the basis of the captured radiographs 10-1 and 10-2 and the spatial poses of the x-ray detectors 4-1 and 4-2 relative to the source position 3. On the basis of the projection, the control device 5 calculates a combined radiograph 12 for the virtual detector plane 11 and, e.g., provides said combined radiograph as a radiograph signal 13, in particular in digital form.

A reconstruction in a computed tomography device can subsequently be implemented on the basis of the radiograph or the combined radiographs 12. Since the x-ray examination arrangement has an effectively larger active detector area than the individual x-ray detectors, a test object can be measured with a higher resolution and/or within a shorter period of time.

Figure 2:
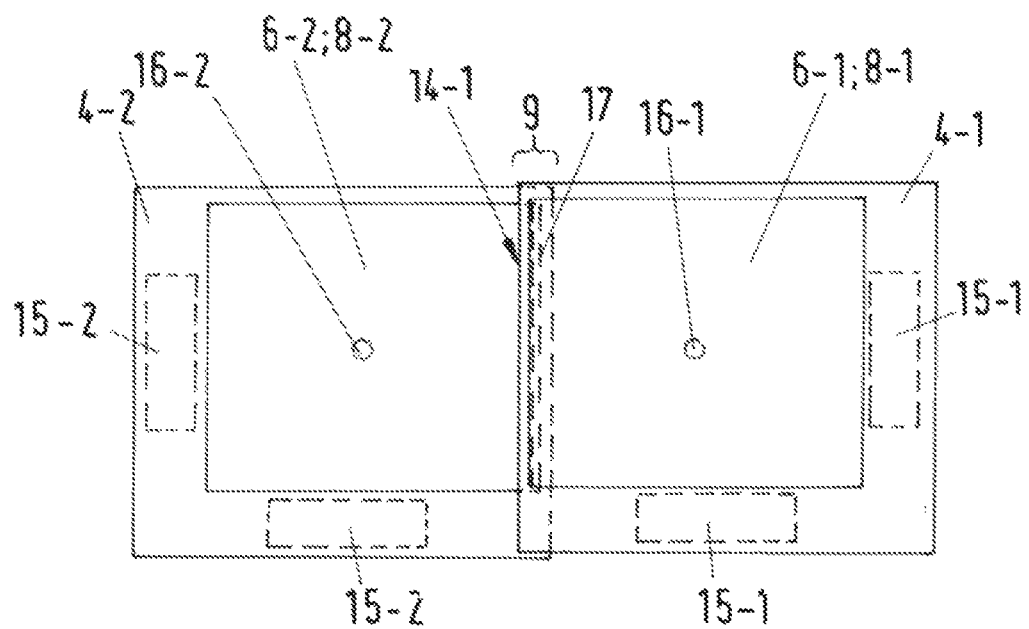
FIG. 2 shows a schematic illustration of the x-ray detectors of the x-ray examination arrangement shown in FIG. 1, from the direction of the source position.

FIG. 2 shows a schematic illustration of the x-ray detectors 4-1 and 4-2 of the x-ray examination arrangement 1 shown in FIG. 1, from the direction of the source position 3. Since the back x-ray detector 4-2 is partly arranged behind the front x-ray detector 4-1, an overlap region 9 arises between the two x-ray detectors 4-1 and 4-2, solid angle ranges 8-1 and 8-2 captured by the active detector areas 6-1 and 6-2 overlapping in said overlap region. The active detector areas 6-1 and 6-2 also overlap in the overlap region 9, and so a portion 17 of the solid angle ranges 8-1 and 8-2 is captured both by the back x-ray detector 4-2 and by the front x-ray detector 4-1.

Since the front x-ray detector 4-1, on account of its active detector area 6-1 and a housing 14-1 extending along the outer edge, attenuates or disturbs x-ray radiation incident on the back x-ray detector 4-2 or on the active detector area 6-2 of the back x-ray detector 4-2 in this region, provision can be made for the control device 5 (FIG. 1) to be configured to correct a disturbance, caused by at least one of the x-ray detectors 4-1 and 4-2 but in particular by the front x-ray detector 4-1, in the captured radiographs 10-1 and 10-2 (FIG. 1) and/or in the combined radiograph 12.

By way of example, a simple correction can be implemented by an "offset/gain" correction ("flat-field correction"). In addition or as an alternative thereto, there can be a model-based correction and/or a correction based on machine learning.

In order to minimize disturbing effects where possible, provision is made, in particular, for the x-ray detectors 4-1 and 4-2 to be arranged relative to one another in such a way that actuation electronics 15-1 and 15-2 of the x-ray detectors 4-1 and 4-2 are arranged outside of the overlap region 9 of the x-ray detectors 4-1 and 4-2. In the shown exemplary embodiment with two x-ray detectors 4-1 and 4-2, the actuation electronics 15-1 of the front x-ray detector 4-1 are arranged on the right and at the lower edge and the actuation electronics 15-2 of the back x-ray detector 4-2 are arranged at the left and at the lower edge. Therefore, only an edge of the active detector area 6-1 and the housing 14-1 of the front x-ray detector 4-1 are arranged in the overlap region 9.

Further, provision can be made, in particular, for the x-ray detectors 4-1 and 4-2 to be arranged in such a way that planes of the x-ray detectors 4-1 and 4-2, which correspond to the active detector areas 6-1 and 6-2, are at an angle with respect to one another. Expressed simply, a plane of the active detector area 6-2 of the back x-ray detector 4-2 is tilted with respect to a plane of the active detector area 6-1 of the front x-ray detector 4-1. In particular, what can be achieved thereby is that x-ray radiation emanating from the x-ray radiation source 2 is incident in perpendicular fashion on the planes or the active detector areas 6-1 and 6-2, at least with respect to a respective centre point 16-1 and 16-2 of said active detector areas 6-1 and 6-2. As a result, a mean effective resolution can be set for each of the x-ray detectors 4-1 and 4-2.

Further, provision can be made for the control device 5 to synchronize the x-ray detectors 4-1 and 4-2 with respect to respective capture times of the radiographs and/or to adapt capture times of pixels in the radiographs. By way of example, a readout process can be started by way of a common trigger signal. By way of example, the adaptation can be implemented on the basis of an interpolation between picture values of a pixel which were captured at adjacent times, i.e., in successive radiographs. As a result, a common effective capture time can be created for all pixels of a radiograph. This procedure is advantageous, particularly when measuring a rotating test object, and facilitates an improved resolution of the captured radiographs and of a three-dimensional reconstruction subsequently calculated therefrom.

Further, provision can be made for the control device 5 to take account of a capture time of pixels of radiographs of the at least two x-ray detectors 4-1 and 4-2 during the projection. This is particularly advantageous in the case of a rotating test object. Therefore, a changing perspective of the test object over the respective capture time can therefore be taken into account during the projection.

Figure 3A:
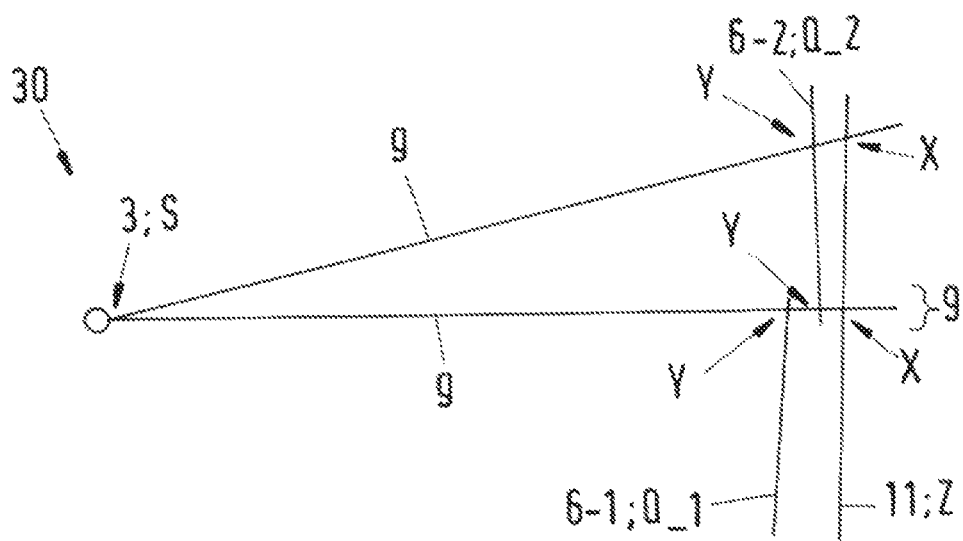
FIG. 3A shows a schematic illustration for elucidating a projection onto the virtual detector plane (plan view) according to an exemplary embodiment of the disclosure.
Figure 3B:
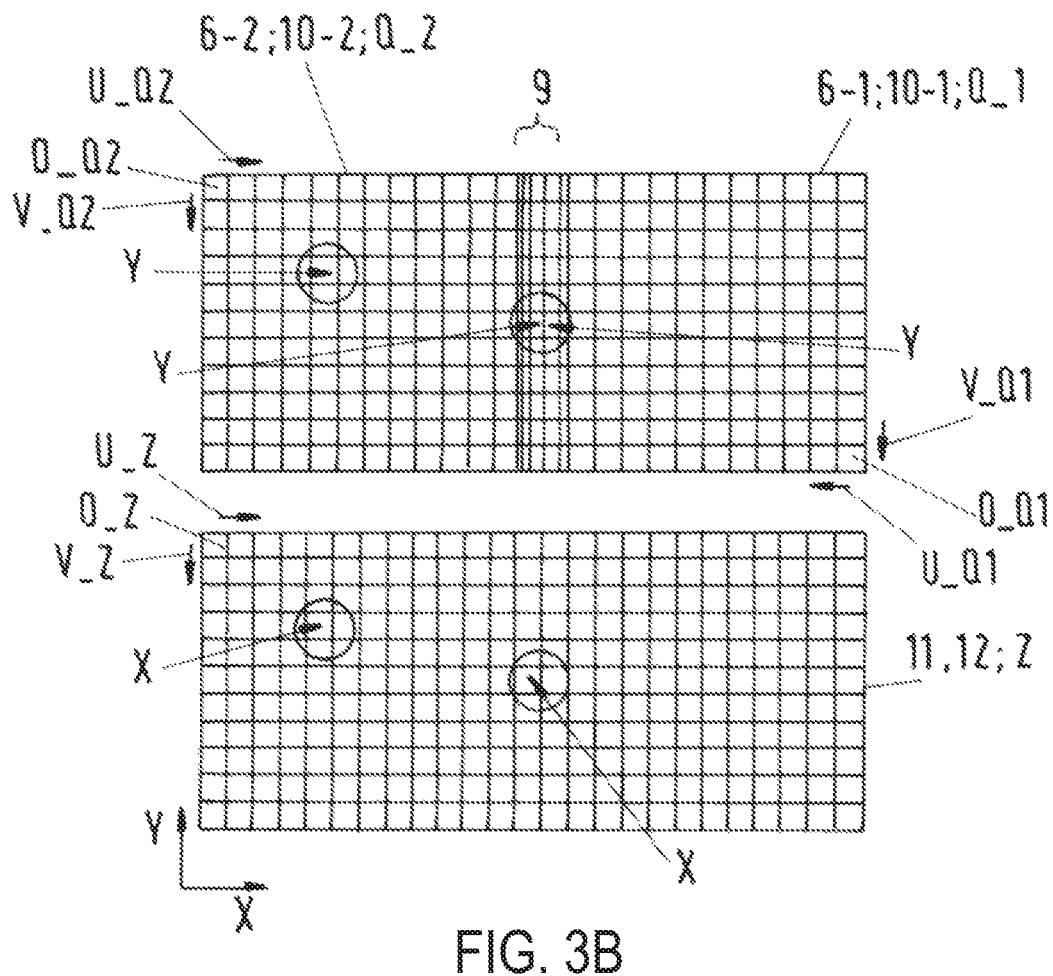
FIG. 3B shows a schematic illustration for elucidating the projection onto the virtual detector plane (view of active detector areas of the x-ray detectors) according to an exemplary embodiment of the disclosure.

FIGS. 3A and 3B show schematic illustrations for elucidating the projection 30 onto the virtual detector plane 11 according to an exemplary embodiment, wherein FIG. 3A shows a plan view of the x-ray examination arrangement (analogous to the illustration shown in FIG. 1) and FIG. 3B shows radiographs 10-1 and 10-2 respectively captured by the active detector areas 6-1 and 6-2 and a combined radiograph 12 in a virtual detector plane 11. The radiographs 10-1, 10-2, and 12 are divided into individual, regular pixels (picture elements).

By way of example, the projection 30 (FIG. 3A) onto the virtual detector plane 11 is carried out as follows: Proceeding from integer pixel coordinates in the virtual detector plane 11 (points of intersection X), these are projected into the plane of the active detector areas 6-1 and 6-2 by a projection straight line g, which extends from a source position 3 to the respective point of intersection X. However, as a rule, non-integer pixel coordinates arise at the points of intersection Y with the active detector areas 6-1 and 6-2, and so an interpolation must be implemented between a plurality of pixels or captured image values of the respectively captured radiographs. The resultant image value then forms the corresponding image value in the combined radiograph, i.e., at the integer pixel coordinate from which the method proceeded. Here, the interpolation allows taking account of or merging of in particular, different scanning (i.e., detector element or pixel sizes) of the x-ray detectors and at the virtual detector plane 11.

A method that is carried out in the control device for projecting the image values of the radiographs 10-1 and 10-2 captured by the x-ray detectors onto image values in the combined radiograph 12 is described below with reference to FIGS. 3A and 3B. The described method is exemplary in this case; in principle, other methods can also be used for the projection.

Below, the x-ray detectors are referred to as source detectors Q_1 and Q_2 within the meaning of sources for the projection. A virtual x-ray detector arranged in the virtual detector plane 11 is referred to as a virtual target detector Z below, within the meaning of a projection target. Further, the assumption is made that both source detectors Q_1 and Q_2 and the virtual target detector Z supply a radiograph 10-1, 10-2, and 12 that is divided into pixels, i.e., picture elements.

In principle, the virtual target detector Z can have any arrangement. The virtual target detector Z is defined by a point in space $O\_Z \in R^3$ (FIG. 3B) which specifies the location of the origin pixel (pixels are punctiform, in particular, in this case) and by two vectors U_Z and V_Z ($\in R^3$) which, proceeding from the origin pixel O_Z, indicate the directions of the x- and y-axis of the detector pixel grid and whose lengths indicate the distance of adjacent pixels; and by the number of the detector pixels in the x-direction nx_Z and in the y-direction ny_Z.

The vectors U_Z and V_Z both lie in a detector plane and span the latter; together with the origin pixel O_Z, they define a pixel grid of the target detector Z. The origin pixel O_Z lies in one corner of the pixel grid, e.g., top left on the target detector Z when the target detector Z is observed from the front, i.e., from a capture direction (cf. FIG. 3B).

A projection into the virtual detector plane 11 requires the presence of a projection center S and one or more physically existing source detectors Q_i, image content of respectively captured radiographs 10-1, 10-2 being transferred from there to a combined radiograph 12 of the virtual target detector Z. In this case, the common projection center S is the source position 3 of the x-ray radiation source (FIG. 3a), which is assumed to be punctiform for this purpose.

Once a projection center S, one or more source detectors Q_i and a virtual target detector Z have been defined, the image content of the target detector Z can be determined as follows:

a. The pixel (picture element) with coordinates (i, j) of the target detector Z has the position:

$$X = O\_Z + i*U\_Z + j*V\_Z$$

Here, i and j are integers and $0 <= i < nx\_Z$ and $0 <= j < ny\_Z$ apply.

b. Determine the straight line g through S and X c. For all source detectors Q_i:
  i. Determine the point of intersection Y of the straight line g with the plane of the source detector Q_i. Since Y lies in the detector plane of Q_i, it is possible to write $$Y = O\_Qi + k*U\_Qi + l*V\_Qi,$$

where O_Qi denotes the location of the origin pixel, and U_Qi and V_Qi denote the spanning vectors of the detector Q_i. k and l denote the location of the point of intersection Y in the pixel grid of Q_i.

ii. If (k>=0) and (l>=0) and (k (nx_Qi−1)) and (1<= (ny_Qi−1)) apply, Y is located within the pixel grid of Q_i. In this case, the image content of Q_i at the pixel coordinate (k, l) can be interpolated by virtue of the pixel values in the neighborhood being suitably taken into account. The following, inter alia, are known as interpolation methods: nearest neighbor interpolation, bilinear interpolation, bicubic interpolation. The image value V_i is obtained as a result of the interpolation.

d. The value of the target pixel can be determined on the basis of the set of image values V_i. There are three possible cases:
  i. {V_i} contains no elements; i.e., the straight line g intersects none of the source detectors within the pixel grid thereof, and no value for the target pixel can be determined.
  ii. {V_i} contains exactly one element: only one source detector contains image content that is mapped onto the target pixel by the projection. The target pixel (i, j) is set to this value V_i.
  iii. {V_i} contains more than one element: at least two source detectors Q_i contain image content (cf., e.g., FIG. 3A: the two points of intersection Y in the overlap region 9) that is mapped onto the target pixel by the projection. In this case, the value of the target pixel is determined as a weighted sum of the values {V_i}. This weighting allows, e.g., a smooth (i.e., for example a linear) transition to be created in the overlap region between the source detectors Q_i.

A definition of the target detector Z in which a pixel value can be interpolated for all target pixels is typical, i.e., in which the straight line g always intersects at least one source detector Q_i within the pixel grid for all target pixels and hence in which an interpolation in the source detector Q_i is possible. Otherwise there are undefined target pixels that cannot be determined from source detector pixel values by interpolation.

It is not necessary to explicitly carry out the determination of the straight line g and of the points of intersection Y of g with the detector planes Q_i for each target pixel. Instead, provision can be made for a 3×3 matrix M_i to be determined, the latter producing the perspective mapping from Z to Q_i. Homogeneous coordinates are used in order to determine the interpolation position in the source detector Q_i for the target pixel (i, j), i.e., (i, j) is augmented to (i, j, 1). This vector is multiplied by the matrix M_i. As a result, the first two coordinates are divided by the third coordinate in order to determine the interpolation position (k, l) for the target detector Q_i.

A pixel size (picture element size) of the target detector Z (i.e., the length of vectors U_Z and V_V) can be chosen freely. Typically, the pixel size is chosen such that the distance between the interpolation positions in the source detectors Q_i corresponds to the pixel size of these x-ray detectors. This ensures that no details are lost when scanning the source detectors Q_i.

Since, in particular, x-ray detectors of the same design are used, the arrangements of the individual pixels may be different in the case of rotated x-ray detectors. In the case of the two source detectors Q_1 and Q_2 shown in FIG. 3B, this is expressed by the fact that the positions of the origin pixels O_Qi are arranged at different corners and the spanning vectors U_Q1 and U_Q2 and V_Q1 and VQ2 respectively point in opposite directions. Should this be necessary, this can be taken into account when projecting by virtue of implementing appropriate conversions.

Figure 4:
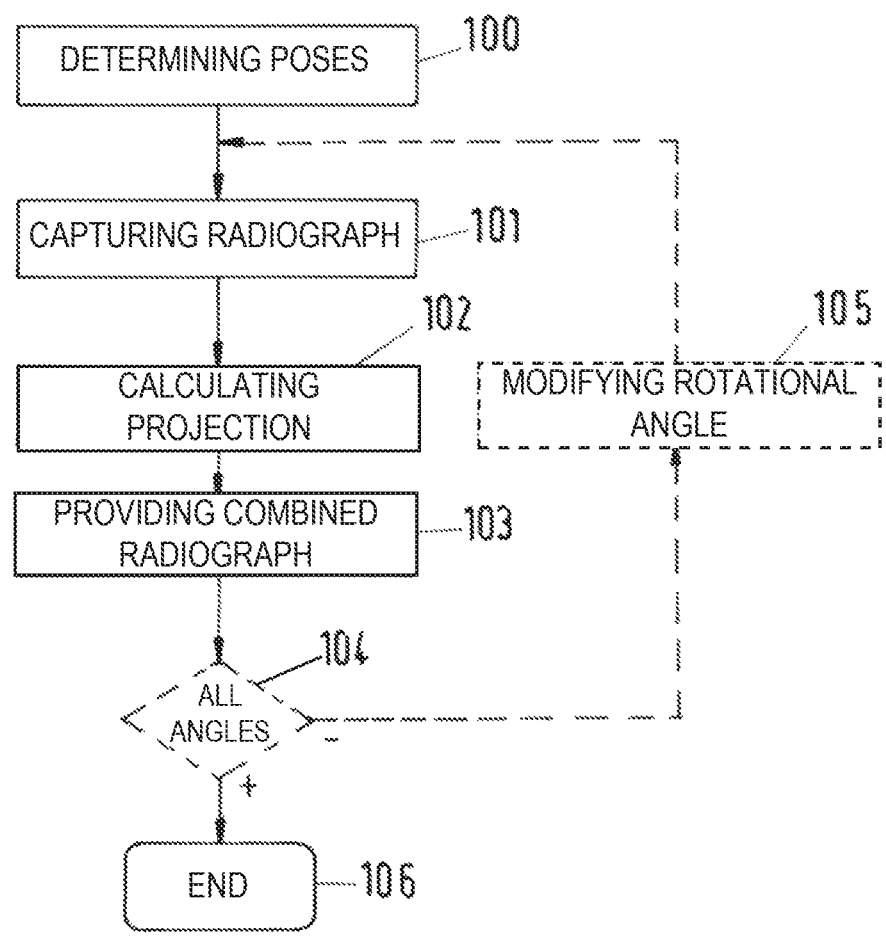
FIG. 4 shows a schematic flow chart of an method for operating an x-ray examination arrangement according to an exemplary embodiment of the disclosure.

FIG. 4 shows a schematic flow chart of an exemplary embodiment of the method for operating an x-ray examination arrangement. The x-ray examination arrangement corresponds, for example, to the exemplary embodiment shown in FIG. 1.

The poses of the two x-ray detectors 4-1 and 4-2 (FIG. 1) are determined in a method step 100, which precedes the actual method. This is implemented with the aid of methods, known per se, for determining a geometry of a beam path in the x-ray examination arrangement or in a computed tomography device. By way of example, in the known methods, a known reference object is examined by the x-ray examination arrangement and a respective spatial pose of the active detector areas of the two x-ray detectors is ascertained relative to a source position of an x-ray radiation source, which serves as a starting point for a projection carried out within the scope of the method.

In a method step 101, a radiograph of a test object is captured by each of the two x-ray detectors.

In method step 101, provision can be made for a disturbance in the captured radiographs, caused by at least one of the x-ray detectors, to be corrected by the control device. By way of example, a simple correction can be implemented by way of an "offset/gain" correction ("flat-field correction").

In addition or as an alternative thereto, there can be a model-based correction and/or a correction based on machine learning.

In a method step 102, a projection onto a virtual detector plane is calculated by the control device of the x-ray examination arrangement on the basis of the respectively captured radiographs and the spatial poses, ascertained in method step 100, of the two x-ray detectors relative to the source position. By way of example, this is implemented with the aid of the method described above. As a result, the projection supplies a combined radiograph that lies in the virtual detector plane. Particularly in this case of the same resolution in respect of a captured solid angle, the combined radiograph is larger than the individual radiographs.

In method step 102, too, provision can be made for a disturbance in the combined radiograph, caused by at least one of the x-ray detectors, to be corrected by the control device.

In a method step 103, the combined radiograph is provided by the control device, for example in the form of a radiograph signal. In particular, the radiographic signal can be available in digital form, for example as a digital data packet. By way of example, the combined radiograph can be used for a three-dimensional reconstruction in a computed tomography device.

Provision can be made for the method to be subsequently repeated. In particular, provision can be made for the method to be repeated for a plurality of rotational angles of a rotary stage of a computed tomography device. Therefore, a check is carried out in a method step 104 as to whether radiographs have already been captured for all the envisaged rotational angles of the rotary stage.

Should this not be the case, the rotational angle of the rotary stage is modified in a method step 105. Following the change in the rotational angle, the test object arranged on the rotary stage is captured again and method steps 101 to 103 are repeated for this rotational angle.

By contrast, if the check in method step 104 yields that method steps 101 to 103 have been run through for all rotational angles, the method is terminated 106.

The combined radiographs can subsequently serve as a basis for a three-dimensional reconstruction of the test object in the computed tomography device.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 X-ray examination arrangement
2 X-ray radiation source
3 Source position
4-1 Front x-ray detector
4-2 Back x-ray detector
5 Control device
6-1 Active detector area
6-2 Active detector area
7 X-ray radiation
8-1 Solid angle range
8-2 Solid angle range
9 Overlap region
10-1 Captured radiograph
10-2 Captured radiograph
11 Virtual detector plane
12 Combined radiograph 13 Radiographs signal
14-1 Housing
14-2 Housing
15-1 Actuation electronics
15-2 Actuation electronics
16-1 Centre point
16-2 Centre point
17 Portion
30 Projection
100-105 Method steps
I, j, k, l Integer indices
Q_i Source detector i
S Projection centre
Z Virtual target detector
O_Z Position of the origin pixel (target detector)
U_Z Spanning vector (target detector)
V_Z Spanning vector (target detector)
nx_Z Number of pixels (picture elements) in the x-direction (target detector)
ny_Z Number of pixels (picture elements) in the y-direction (target detector)
V_i Image value
{V_i} Set of the image values ascertained during the projection
O_Qi Position of the source pixel (source detector i)
U_Qi Spanning vector (source detector i)
V_Qi Spanning vector (source detector i)
nx_Qi Number of pixels (picture elements) in the x-direction (source detector i)
ny_Qi Number of pixels (picture elements) in the y-direction (source detector i)
X Point of intersection (position of the target pixel)
Y Point of intersection (position of the source pixel)
g Projection straight line

What is claimed is:

1. An x-ray examination arrangement comprising:
an x-ray radiation source arranged at a source position;
at least two x-ray detectors having active detector areas and being arranged such that the active detector areas capture different solid angle ranges with respect to x-ray radiation produced by the x-ray radiation source and emanating from the source position; and
a control device configured to:
calculate a projection onto a virtual detector plane based on radiographs respectively captured by the at least two x-ray detectors and spatial poses of the at least two x-ray detectors relative to the source position, and
provide a combined radiograph for the virtual detector plane based on the projection,
wherein the projection is a perspective projection onto the virtual detector plane,
wherein the perspective projection onto the virtual detector plane is implemented with reference to a projection straight line emanating from the source position by virtue of an image value at a point of an intersection of the projection straight line with the at least two x-ray detectors being determined, and
wherein the determined image value is subsequently projected onto the virtual detector plane along the projection straight line.

2. The x-ray examination arrangement according to claim 1, wherein the at least two x-ray detectors at least partly overlap in relation to a propagation direction of the x-ray radiation.

3. The x-ray examination arrangement according to claim 2, wherein:
the at least two x-ray detectors include actuation electronics, and
the at least two x-ray detectors are arranged relative to one another such that the actuation electronics are arranged outside of an overlap region of the at least two x-ray detectors.

4. The x-ray examination arrangement according to claim 1, wherein the at least two x-ray detectors are arranged such that planes of the at least two x-ray detectors have an angle with respect to one another, said planes corresponding to the active detector areas, and/or such that the x-ray radiation emanating from the x-ray radiation source is incident on the planes or the active detector areas in perpendicular fashion, at least in relation to a center point of the active detector areas.

5. The x-ray examination arrangement according to claim 1, wherein the control device is configured to correct a disturbance, caused by at least one of the at least two x-ray detectors, in the radiographs and/or in the combined radiograph.

6. The x-ray examination arrangement according to claim 1, wherein the control device is further configured to synchronize the at least two x-ray detectors in relation to respective capture times of the radiographs and/or to adapt capture times of pixels in the radiographs.

7. The x-ray examination arrangement according to claim 1, wherein the control device is configured to take a capture time of pixels of radiographs of the at least two x-ray detectors into account during the projection.

8. The x-ray examination arrangement according to claim 1, wherein the control device is further configured to set a pixel size in the combined radiograph.

9. A computed tomography device comprising at least one x-ray examination arrangement according to claim 1, wherein the computed tomography device is configured to carry out a reconstruction, at least in part based on the combined radiograph.

10. Method for operating an x-ray examination arrangement, the x-ray examination arrangement including an x-ray radiation source arranged at a source position, at least two x-ray detectors, and a control device, the method comprising:
arranging the at least two x-ray detectors such that active detector areas of the at least two x-ray detectors capture different solid angle ranges with respect to x-ray radiation produced by the x-ray radiation source and emanating from the source position;
calculating, by the control device, a projection onto a virtual detector plane based on radiographs respectively captured by the at least two x-ray detectors and spatial poses of the at least two x-ray detectors relative to the source position; and
providing a combined radiograph for the virtual detector plane based on the projection,
wherein the projection is a perspective projection onto the virtual detector plane,
wherein the perspective projection onto the virtual detector plane is implemented with reference to a projection straight line emanating from the source position by virtue of an image value at a point of an intersection of the projection straight line with the at least two x-ray detectors being determined, and
wherein the determined image value is subsequently projected onto the virtual detector plane along the projection straight line.

* * * * *